Figure 1:
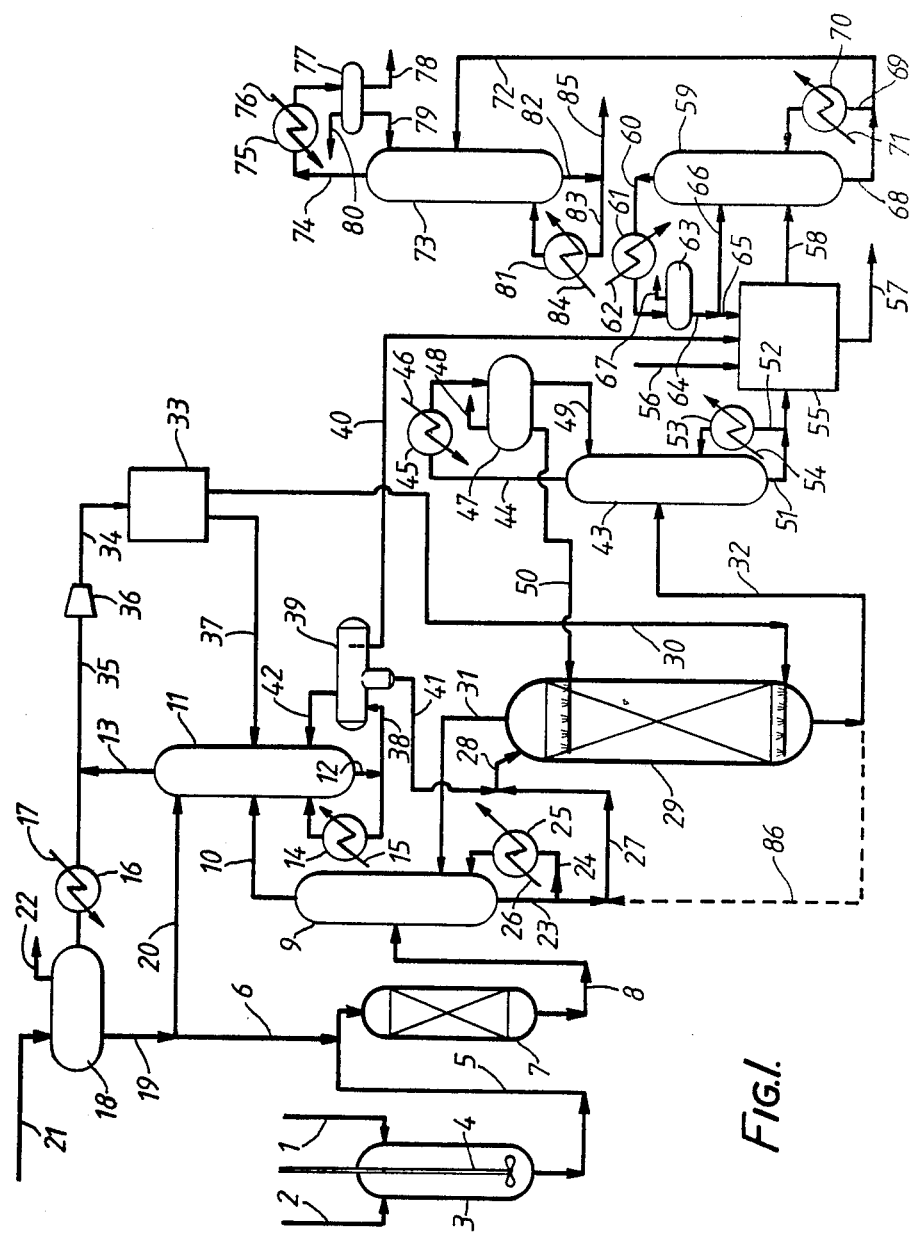

United States Patent [19]

Kippax et al.

[11] Patent Number: 4,795,824
[45] Date of Patent: Jan. 3, 1989

[54] PROCESS FOR THE PRODUCTION OF DIALKYL MALEATES

[75] Inventors: John W. Kippax, Bedale; Colin Rathmell, Yarm, both of England

[73] Assignee: Davy McKee (London) Limited, London, England

[21] Appl. No.: 80,060

[22] Filed: Jul. 31, 1987

[30] Foreign Application Priority Data

Aug. 1, 1986 [GB] United Kingdom ............... 8618888

[51] Int. Cl.$^4$ .............................................. C07C 67/03
[52] U.S. Cl. ..................... 560/204; 203/14; 203/DIG. 2; 203/DIG. 11; 502/11; 560/191; 562/595
[58] Field of Search ............... 560/204, 191; 562/595; 502/11; 203/14, 2, 11

[56] References Cited

U.S. PATENT DOCUMENTS

| | | | |
|---|---|---|---|
| 3,862,147 | 1/1975 | Cooley et al. | 560/204 X |
| 3,886,199 | 5/1975 | Suter et al. | 560/204 X |
| 4,032,458 | 6/1977 | Cooley et al. | 60/190 X |
| 4,314,947 | 2/1982 | Hohenschultz et al. | 260/410 |
| 4,361,710 | 11/1982 | Weitz et al. | 568/864 |
| 4,481,146 | 11/1984 | Leupold et al. | 260/410 |
| 4,562,283 | 12/1985 | Schnabel et al. | 560/204 |

FOREIGN PATENT DOCUMENTS 0143634 5/1985 European Pat. Off. .

Primary Examiner—Werren B. Lone
Assistant Examiner—Vera C. Clarke
Attorney, Agent, or Firm—Bernard, Rothwell & Brown

[57] ABSTRACT

A process is described for the production of a dialkyl maleate by reaction of maleic anhydride with an alkyl alcohol in a monoesterification zone to form the corresponding monoalkyl maleate, followed by reaction of resulting monoalkyl maleate with further alkyl alcohol to form the corresponding dialkyl maleate, which includes the steps of supplying a first liquid feed comprising said monoalkyl maleate to a secondary esterification zone containing a charge of a solid esterification catalyst, supplying a second feed stream comprising said alkyl alcohol to said secondary esterification zone, maintaining said secondary esterification zone at an elevated temperature sufficient to form or to maintain therein a vaporous stream containing said alkyl alcohol, intimately contacting said first liquid feed in said secondary esterification zone in the presence of said catalyst with said vaporous feed stream, recovering from said secondary esterification zone a vaporous effluent stream containing, in addition to alkyl alcohol vapor, also water in vapor form, said water being produced in said secondary esterification zone by esterification of said monoalkyl maleate with said alkyl alcohol, and recovering from said secondary esterification zone a liquid product stream containing said dialkyl maleate.

34 Claims, 6 Drawing Sheets

PROCESS FOR THE PRODUCTION OF DIALKYL MALEATES

This invention relates to a process for the production of dialkyl maleates.

The production of dialkyl maleates by esterification of maleic anhydride, of maleic acid or of a mixture containing both maleic anhydride and maleic acid has been described on many occasions in the literature. As maleic acid is dibasic, esterification proceeds stepwise via the monoalkyl maleate. In the case of maleic anhydride this stepwise esterification can be described by the equations:

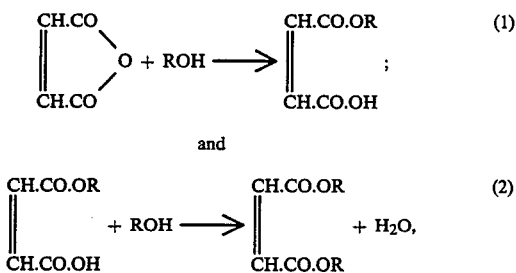

and $$\begin{array}{c} CH.CO.OR \\ \| \\ CH.CO.OH \end{array} + ROH \longrightarrow \begin{array}{c} CH.CO.OR \\ \| \\ CH.CO.OR \end{array} + H_2O, \quad (2)$$

where R is an alkyl group. These reactions can be carried out in two substantially separate steps in separate reactors or simultaneously in a single reactor. The monoesterification step of equation (1) can be effected non-catalytically, conveniently by use of elevated temperatures. The diesterification step of equation (2) can likewise be carried out non-catalytically; however, it is usually preferred to use an esterification catalyst in the diesterification step of equation (2), such as an acid catalyst (e.g. sulphuric acid).

Diethyl maleate is produced as a fine chemical on a commercial scale, usually by a batch reaction process. In this known process maleic anhydride or a mixture of maleic anhydride and maleic acid, in either case possibly containing a minor amount of fumaric acid, is reacted with excess ethanol in the presence of a homogeneous liquid phase esterification catalyst, such as sulphuric acid or a derivative thereof. The reaction conditions are generally selected so as to cause substantially all of the maleic anhydride to react. However, as the diesterification reaction of equation (2) above is reversible, the reaction product does not yield solely the desired diethyl maleate; usually the reaction yields at most about 95 mole % diethyl maleate, the balance comprising mainly monoethyl maleate, besides smaller amounts of monoethyl fumarate, diethyl fumarate, maleic acid and fumaric acid. The reaction mixture also contains excess ethanol and water produced by the esterification of the mono-esters formed as intermediates, i.e. monoethyl maleate and monoethyl fumarate.

In order to recover the dialkyl maleate product the catalyst must first be removed, prior to attempting purification by distillation techniques, by neutralisation with alkali and then washing with water. These neutralisation steps produce significant quantities of aqueous liquors and remove not only the catalyst but also any monoalkyl maleate and any other acid materials present, such as traces of unreacted maleic anhydride or maleic acid.

In addition, as diethyl maleate is somewhat soluble in water, some of the desired diethyl maleate product is lost, together with the acidic materials, in the wash liquor. Although it would be theoretically possible to recover the monoalkyl maleate from the resulting aqueous liquors and to recycle this to the process for the production of further dialkyl maleate, this is not economically feasible. Hence the monoalkyl maleate is lost to the process in these aqueous liquors which are a potential pollution hazard. Moreover the loss of monoalkyl maleate and disposal of these waste liquors represent a significant operating cost.

Similar procedures can be used for batch production of other dialkyl maleates using other alkyl alcohols in place of ethanol.

Although it would be possible to adapt this known process for continuous operation with relatively simple modifications thereof, the resulting process would still suffer from the drawback of significant loss of potential product, in the form of monoalkyl maleate and of the other organic acid materials present in the reaction product mixture. Moreover, as the acid catalyst is destroyed in the product recovery steps, the consumption of sulphuric acid or derivative thereof would add to the cost of operation of a large scale continuously operating plant.

A further disadvantage of the known process is the risk of contamination of the dialkyl maleate product with sulphur-containing impurities, which may rule out its use for some purposes, for example as a feedstock for hydrogenation to yield butane-1,4-diol, tetrahydrofuran and/or gamma-butyrolactone. Further teaching regarding use of dialkyl maleates (such as, for example, diethyl maleate) for this purpose can be obtained, for example, from EP-A-No. 0143634, from WO-A-B No. 6/O3189 or from WO-A-B No. 86/07358. As the catalysts used for such duty are poisoned by the presence of sulphur-containing compounds in the feedstock ester (or in the hydrogen-containing gas), stringent purification measures may be required in order to reduce the sulphur content of the ester to an acceptably low level. Such additional purification steps add significantly to production costs.

Various proposals which avoid the use of catalysts have been described. Thus U.S. Pat. No. 4,361,710 proposes washing a gaseous mixture containing maleic anhydride with a monohydric or polyhydric alcohol boiling above 180° C. (e.g. 2-ethylhexanol or dodecan-1-ol) to form a solution of the corresponding maleic acid half-ester in the alcohol followed by heating the solution to remove water and to form a solution of maleic acid diester in the alcohol. As water boils at a temperature well below that of the alcohol it is readily removed from the reaction mixture, thus enabling the diesterification reaction to be driven to completion.

U.S. Pat. No. 4,032,458 describes a process for the production of 1,4-butanediol in which maleic acid is esterified at elevated temperature and pressure and then subjected to a two step hydrogenation procedure. According to the description of the drawing it is preferred to use for esterification a monohydric alcohol which forms a heterogeneous azeotrope with water, such as n-butanol. The esterification step is carried out in a distillation zone from which an n-butanol-water azeotrope is removed overhead. According to column 11, lines 23 to 27, this azeotrope is condensed and allowed to separate into two layers. The n-butanol layer is decanted, redistilled, and recycled to the distillation zone. The n-butanol-water azeotrope has a boiling point (92.7° C. at atmospheric pressure) which is appreciably lower than the boiling point of the alcohol itself (117.4° C. at atmospheric pressure), thus permitting the water to be removed readily from the esterification mixture. In addition the process can only operate as described because the condensed azeotrope is heterogeneous and separates into two layers, thus permitting ready recovery of n-butanol for recycle to the process.

Although it is stated at column 8, lines 45 to 47 of U.S. Pat. No. 4,032,458 that:

"Other suitable monohydric alcohols useful in the process of their invention include ethanol, propanol, butanol, amylalcohol and the like", the illustrated form of plant will not operate with ethanol in place of n-butanol because ethanol is fully miscible with water and forms therewith a homogeneous azeotrope comprising a single liquid phase. It requires much energy to produce substantially dry ethanol from this azeotrope for recycle to the process. Moreover, because the boiling point of the ethanol-water azeotrope is extremely close (78.17° C. at atmospheric pressure) to that of ethanol itself (78.32° C. at atmospheric pressure) all the ethanol must be distilled out of the esterification mixture in order to remove all the water. n-propanol gives rise to similar problems. Because of these factors it is extremely costly in energy requirements, when using ethanol or propanol in the distillation-esterification step of the process of U.S. Pat. No. 4,032,458, to remove the water of esterification completely and hence drive the esterification reaction towards production of a 100% yield of dialkyl maleate.

U.S. Pat. No. 4,562,283 discloses a method of separating maleic anhydride from gaseous reaction mixtures by contact in the bottom of a column with butanol and then washing the treated gases in the column with a countercurrent stream of butyl maleate. According to column 2, lines 33 to 36 of U.S. Pat. No. 4,562,283, any water formed is removed from the column above the feed point for the butanol. Again, this procedure can be used for removal of the water of esterification only because the butanol-water azeotrope boils appreciably below butanol itself and because the azeotrope separates into two liquid phases upon condensation.

There is accordingly a need to provide a process for the production of dialkyl maleates from maleic anhydride and mixtures thereof with maleic acid in which consumption of acid catalyst is substantially obviated. Additionally there is a need to provide a process, which can be operated continuously for producing a dialkyl maleate with high process efficiency and without substantial losses of intermediate monoalkyl maleate in the product recovery stages. Yet a further need is to provide a process which avoids the risk of contamination of the dialkyl maleate product with sulphur-containing compounds.

The present invention accordingly seeks to provide a process for the production of a dialkyl maleate in which substantially complete conversion of maleic anhydride or a mixture of maleic anhydride and maleic acid to a dialkyl maleate is achieved. It further seeks to provide a continuously operable process for the production of dialkyl maleates from maleic anhydride and the corresponding alkyl alcohol without consumption of catalyst. In addition it seeks to provide a process in which the use of sulphuric acid and its derivatives as homogeneous catalysts in the esterification of the monoalkyl maleate is avoided thereby obviating the risk of contamination of the product dialkyl maleate.

According to the present invention there is provided a process for the production of a dialkyl maleate by reaction of maleic anhydride with an alkyl alcohol in a monoesterification zone to form the corresponding monoalkyl maleate, followed by reaction of resulting monoalkyl maleate with further alkyl alcohol to form the corresponding dialkyl maleate, which includes the steps of supplying a first liquid feed comprising said monoalkyl maleate to a secondary esterification zone containing a charge of a solid esterification catalyst, supplying a second feed stream comprising said alkyl alcohol to said secondary esterification zone, maintaining said secondary esterification zone at an elevated temperature sufficient to form or to maintain therein a vaporous stream containing said alkyl alcohol, intimately contacting said first liquid feed in said secondary esterification zone in the presence of said catalyst with said vaporous stream, recovering from said secondary esterification zone a vaporous effluent stream containing, in addition to alkyl alcohol vapour, also water in vapour form, said water being produced in said secondary esterification zone by esterification of said monoalkyl maleate with said alkyl alcohol, and recovering from said secondary esterification zone a liquid product stream containing said dialkyl maleate.

The process may include use of a single secondary esterification zone; often, however, it will be preferred to operate using a plurality of secondary esterification zones connected in series.

In the process of the invention the first liquid feed supplied to the secondary esterification zone (or to the first of the secondary esterification zones, if two or more such zones in series are used) contains monoalkyl maleate. This first liquid feed may, under suitable circumstances, comprise the reaction product from the monoesterification zone. Thus if, for example, a substantially 1:1 maleic anhydride:alkyl alcohol molar ratio is used in the monoesterification zone and the reaction proceeds to completion, then the resulting substantially pure monoalkyl maleate can be used directly as the first liquid feed to the secondary esterification zone, or to the first of the secondary esterification zones if more than two such zones in series are used. Normally, however, it will be preferred to utilise excess alkyl alcohol in the monoesterification zone; in this case, if a small excess only of alkyl alcohol is used in the monoesterification zone, then the resulting mixture of monoalkyl maleate and alkyl alcohol can be used as the first liquid feed to the secondary esterification zone (or to the first of such zones if more than one is used). Preferably, however, the first liquid feed to the secondary esterification zone (or to the first such zone) comprises a mixture of monoalkyl maleate and dialkyl maleate. Such a mixture can be obtained by passage of the monoesterification product mixture, possibly after admixture of further alkyl alcohol therewith, through a primary esterification zone containing a charge of a solid esterification catalyst, such as an ion exchange resin containing acidic substituents selected from sulphonic acid groups and carboxylic acid groups. By passage of a mixture of monoalkyl maleate and alkyl alcohol therethrough in co-current, at least a proportion of the monoalkyl maleate is converted in such a primary esterification zone to dialkyl maleate. In this case at least a major part of the water of esterification present in the primary esterification product is preferably removed therefrom, for example by distillation, to yield an ester feedstock which can be used as the first liquid feed to the secondary esterification zone, or to the first of a plurality of such zones connected in series.

It will be seen that water of esterification is removed as vapour from the, or from each, secondary esterification zone by stripping with a stream of alkyl alcohol vapour. The second feed stream comprising said alkyl alcohol can be supplied in liquid form to the or each secondary esterification zone and vaporised therein. Often however, it is supplied thereto in vapour form.

Thus, each secondary esterification zone can be operated in batch mode. For large scale production, however, it will more usually be operated continuously; in this case said first liquid feed is continuously supplied to the or each secondary esterification zone and said liquid product is continuously recovered therefrom.

The rate of supply of the second feed stream comprising said alkyl alcohol as, or to form, the vaporous stream in the or each secondary esterification zone in the process of the invention should be such as to establish and maintain a sufficient concentration of reactant alkyl alcohol in the liquid phase to drive the mono- to dialkyl maleate esterification reaction towards completion and to strip a major part, preferably substantially all, of the water of esterification released by means of this reaction in the respective secondary esterification zone from the liquid phase. The lower the concentration of water in the second feed stream is, the more efficient will be the degree of stripping of product water from the respective secondary esterification zone and the higher will be the conversion to dialkyl maleate. If a second feed stream comprising "dry" alkyl alcohol is used with a water content of, for example, about 1 mole % or less, then it is possible to operate the process so that the liquid product stream comprises at least about 95 mole % of dialkyl maleate, and often at least about 97 mole %, e.g. 99 mole % or more of dialkyl maleate. On the other hand, if the water content of the second feed stream is in the region of about 10 mole %, then the dialkyl maleate content of the liquid product stream will be correspondingly lower, e.g. about 80 mole % up to about 85 mole %.

The maleic anhydride used in the process of the invention may be a substantially pure grade of maleic anhydride. Alternatively it may comprise a mixture of maleic anhydride and maleic acid, containing preferably a major molar amount of maleic anhydride and a minor molar amount of maleic acid. Typically, if a mixture of maleic anhydride and maleic acid is used, this contains at least about 80 mole % of maleic anhydride and not more than about 20 mole % of maleic acid. It may further contain a minor amount, usually from about 0.001 mole % up to about 5 mole %, of fumaric acid. The higher the maleic acid content is, the larger is the amount of water that will be produced in the monoesterification zone.

As a heterogeneous esterification catalyst is used, the catalyst remains in the or each secondary esterification zone. Thus the liquid product therefrom is essentially free from sulphurous impurities introduced as a result of interaction with the catalyst and can be subjected to conventional distillation or similar techniques in order to recover the product dialkyl maleate without having to neutralise the catalyst.

In one preferred process the second feed stream to the secondary esterification zone, if there is only one such zone, or to the final secondary esterification zone, if more than one such zone is used, contains less than about 1 mole % of water.

In one form of the process the secondary esterification zone comprises a reactor containing a charge of an immobilised ion exchange resin containing acidic groups selected from sulphonic acid groups and carboxylic acid groups. Such immobilised ion exchange resin may comprise, for example, packages wrapped in wire mesh, each containing a quantity of beads of said resin. Alternatively the resin may be trapped as beads in wire baskets. It is also envisaged that the resin may be in the form of fibres; in this case the fibres ca be woven into appropriate form or interwoven with wire mesh.

In this form of the process the first liquid feed is conveniently passed downward through the reactor countercurrently to an ascending vaporous stream containing alkyl alcohol vapour. Preferably the reactor is operated as a flooded bubble reactor. As the resin is immobilised in the reactor of the secondary esterification zone, the downflowing liquid passes downwards through regions which are progressively drier and drier against an upflowing stream of bubbles of alkyl alcohol vapour which carry away water of esterification as it is formed. At the bottom end of the reactor the water concentration is lowest and is largely determined by the water content of the second feed stream and its rate of supply. By maintaining the water content of the second feed stream at or below about 1 mole % water, extremely efficient conversion to dialkyl maleate can be achieved in the secondary esterification zone.

The invention further provides a process in which a plurality of secondary esterification zones connected in series are used, each said secondary esterification zone comprising a reactor, typically a stirred tank reactor, containing a charge of an ion exchange resin containing acidic groups selected from sulphonic acid groups and carboxylic acid groups; in such a process it will usually be preferred to arrange that the water content of the second feed stream to the final secondary esterification zone is lower than the corresponding water content of the respective second feed stream to any preceding secondary esterification zone. This may be achieved in an arrangement in which the water content of the second feed stream supplied to each reactor decreases progressively from one reactor to the next in the series. One way in which this can be effected in practice is to arrange that the second feed stream to the, or to each, reactor preceding the final reactor comprises material of the vaporous effluent stream from the next succeeding reactor. In this process it is preferred that the second feed stream to the final secondary esterification zone comprises "dry" alkyl alcohol, typically with a water content of not more than about 1 mole %.

In the first step of the process of the invention maleic anhydride is reacted with an alkyl alcohol to form the corresponding monoalkyl maleate according to the following equation:

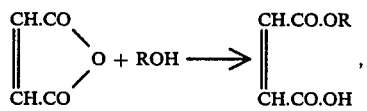

where R is an alkyl radical containing, for example, 1 to 4 carbon atoms. This reaction does not require the presence of a catalyst. Although an equimolar mixture of maleic anhydride and alkyl alcohol can be used, it is preferred to operate using an excess of alkyl alcohol. Thus the maleic anhydride:alkyl alcohol molar ratio may vary within wide limits, but is typically from about 1:1 to about 1:10. Usually, however, it will be preferred to operate with such a molar ratio in the range of from about 1:1.5 to about 1:5, e.g. about 1:2.

The alkyl alcohol fed to the monoesterification zone may contain water recycled from a downstream stage of the process. Dialkyl maleate and maleic anhydride recovered from downstream stages of the process may also be recycled to the monoesterification zone.

The alkyl alcohol used in the process may contain, for example, from 1 to 4 carbon atoms. Examples of suitable alkyl alcohols include methanol, n-propanol, iso-propanol, n-butanol, and iso-butanol. Especially preferred for use in the process of the invention is ethanol.

The product of the process is accordingly preferably the corresponding di- $C_1$ to $C_4$ alkyl maleate. Typical examples are dimethyl maleate, di-n-propyl maleate, di-iso-propyl maleate, di-n-butyl maleate, and di-iso-butyl maleate. The product of the especially preferred process is diethyl maleate.

The monoesterification step can be effected as a batch process but is preferably conducted as a continuous process. In the monoesterification step the temperature is typically from about 50° C. to about 150° C., e.g. about 60° C. to about 100° C., while the pressure is sufficient to maintain the alkyl alcohol in the liquid phase. Typically this is in the range of from about 1 bar up to about 5 bar absolute.

The monoesterification zone may comprise any convenient form of reactor, e.g. a stirred tank reactor. The reaction mixture is generally retained in the monoesterification zone for a predetermined time, typically of the order of from about 15 minutes to about 300 minutes or more, e.g. about 60 minutes. The residence time is selected to permit substantially complete reaction of maleic anhydride and the alkyl alcohol under the chosen reaction conditions to form the corresponding monoalkyl maleate. Hence the reaction mixture from the monoesterification zone comprises monoalkyl maleate, usually also excess alkyl alcohol, and a minor amount only of unreacted maleic anhydride (usually about 0.5 mole % or less), besides possibly also some water, dialkyl maleate, monoalkyl fumarate, diethyl fumarate, maleic acid, and/or fumaric acid.

This monoesterification mixture is passed forward for catalytic conversion to the corresponding dialkyl maleate, possibly after addition of further alkyl alcohol, according to the equation:

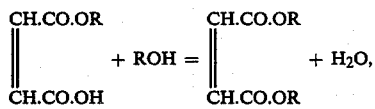

where R is as defined above. This reaction is an equilibrium reaction. Hence, in order to maximise production of dialkyl maleate, it is necessary to remove the water formed in the esterification reaction.

In a preferred continuous process according to the invention a first liquid feed stream containing monoalkyl maleate is passed through at least one secondary esterification zone and is intimately contacted therein with a stream of alkyl alcohol vapour in the presence of a solid esterification catalyst. The first liquid feed stream to the secondary esterification zone, if there is only one such zone, or to the first secondary esterification zone, if there are two or more such zones, may comprise essentially only monoalkyl maleate. Alternatively it may comprise a mixture of monoalkyl maleate and alkyl alcohol. Usually, however, it will be preferred to utilise a mixed feed stream containing both monoalkyl maleate and dialkyl maleate; such a mixed feed stream can be obtained by passing a mixture of monoalkyl maleate and alkyl alcohol, usually in molar excess of that required to effect esterification of the monoalkyl maleate, in co-current through a primary esterification zone which contains a charge of a solid esterification catalyst and is maintained under esterification conditions. Such esterification conditions will normally include use of an elevated temperature in the intermediate esterification zone, as well as use of a pressure sufficient to maintain the alkyl alcohol in the liquid phase. The resulting primary esterification product mixture contains a mixture of mono- and dialkyl maleates, typically in the mole ratio of from about 70:30 to about 20:80, in addition to excess alkyl alcohol and water produced in the esterification reaction and minor amounts of by-products, such as maleic acid, fumaric acid, and mono- and dialkyl fumarates. Preferably the residence time in the primary esterification zone is so selected in relation to the temperature and pressure conditions therein that the primary esterification product mixture is substantially an equilibrium mixture.

Examples of suitable solid esterification catalysts include ion exchange resins, preferably macroreticular ion exchange resins, containing sulphonic acid groups and/or carboxylic acid groups.

Typical reaction conditions in the primary esterification zone include use of a temperature in the range of from about 80° C. to about 140° C., preferably about 100° C. to about 125° C. and of a pressure in the range of from about 1 to about 20 bar, preferably about 5 to about 15 bar. The liquid hourly space velocity through the primary esterification zone preferably ranges from about 0.25 $hr^{-1}$ to about 5 $hr^{-1}$, typically about 1 $hr^{-1}$ to about 2 $hr^{-1}$.

The primary esterification product mixture is free from added catalyst and hence can be distilled without disturbing significantly the reaction equilibrium under normal, reduced or increased pressure, in order to separate alkyl alcohol and water, which are recovered overhead, from an ester-containing mixture containing both mono- and dialkyl maleates. The alkyl alcohol distillate can, possibly after suitable treatment to remove water therefrom, be used as a feedstock for the production of the second feed stream to the secondary esterification zone (if there is only one such zone) or to one (usually the final one) of the secondary esterification zones (if there is more than one such zone). This distillate can also serve as a source of alkyl alcohol for use in the monoesterification zone or in the primary esterification zone. The ester-containing mixture resulting from distillation of the primary esterification product mixture can be used as such as the feed stream to the secondary esterification zone of the process of the invention or can be admixed first with alkyl alcohol, with an inert diluent and/or with material recycled from downstream in the process.

The final product mixture from the secondary esterification zone, if there is only one secondary esterification zone, or from the final secondary esterification zone, if there is more than one such zone, contains predominantly dialkyl maleate. The proportion of dialkyl maleate is, as already mentioned, dependent on the water content of the second feed stream. When a stream comprising "dry" alkyl alcohol containing, for example, less than about 1 mole % water is used as the second feed stream, then the liquid product stream from the secondary esterification zone, if there is only one such zone, or from the final secondary esterification zone, if there is more than one such zone, typically contains dialkyl maleate in an amount of at least about 97 mole % up to about 99 mole % or more, as well as alkyl alcohol, and small amounts of water, maleic acid, and monoalkyl maleate. In some cases traces of fumaric acid and of monoalkyl fumarate can be detected. This final product mixture can be distilled to produce a dialkyl maleate rich product which is free from catalyst and can be used for some purposes as obtained. Alternatively, this catalyst free product can be further purified. If desired, the purification steps may include washing with aqueous alkali or, preferably, with an aqueous wash liquor which contains an alkali metal hydroxide, carbonate, bicarbonate, or a mixture of two or more thereof dissolved in an aqueous solution of the corresponding di-(alkali metal) salt of maleic acid and then with water, followed by one or more distillation steps.

The preferred alkyl alcohol is ethanol and the preferred dialkyl maleate is diethyl maleate.

The cost of producing "dry" ethanol from a "wet" ethanol stream is appreciable. Moreover, it will usually be desirable upon economic grounds to recycle ethanol present in the vaporous effluent stream from the, or from each, secondary esterification zone and in other available streams, for example from a downstream hydrogenation step utilising the process of EP-A-No. 0143634, of WO-A-No. 86/03189 or of WO-A-No. 86/07358, for production of further diethyl maleate. Hence in some cases it may be decided that it is uneconomic to produce "dry" ethanol, e.g. with a water content of no more than about 1 mole %. In this case available ethanol-containing streams may contain from about 2 mole % up to about 10 mole % or more, e.g. up to about 15 mole % of water. Such ethanol containing streams can be utilised as the second feed stream but in this case it will usually suffice to utilise a single secondary esterification zone, e.g. a stirred tank reactor, containing a charge of an ion exchange resin containing sulphonic acid and/or carboxylic acid groups. The diethyl maleate content of the liquid product stream will in this case usually be significantly lower than in the case that "dry" ethanol is used, either in a single reactor with an immobilised ion exchange resin or in a plurality of stirred tank reactors connected in series. Hence, under these circumstances, the diethyl maleate content of the liquid product may be from about 75 mole %, usually at least about 80 mole %, up to about 85 mole % or so, and typically not more than about 90 mole %.

When a stream comprising "wet" ethanol is used as the second feed stream, for example a stream containing from 2 mole % up to about 10 mole % water, then the final product mixture may contain, for example, from about 75 mole % up to about 90 mole %, e.g. about 80 mole % to about 85 mole %, dialyl maleate with the balance comprising monoalkyl maleate, water, maleic acid, fumaric acid, monoalkyl fumarate and dialkyl fumarate. Advantageously such a liquid product stream is further purified.

In a preferred process for the production of diethyl maleate, maleic anhydride and ethanol, preferably in molar excess, are reacted in the monoesterification zone to yield a mixture of monoethyl maleate and ethanol. This is preferably admixed with a further quantity of ethanol and passed to a primary esterification zone, which contains a charge of a solid esterification catalyst, such as an ion exchange resin of the type mentioned above. The primary esterification zone can take the form of a trickle bed reactor or a stirred tank reactor or a resin packed column.

The resulting mixture of monoethyl maleate, diethyl maleate, ethanol and water (and possibly also minor amounts of impurities) is then distilled in a first distillation zone to yield an ethanol/water mixture, containing also a minor amount of diethyl maleate, as overhead product, and an ester-containing product containing, typically, an approximately 70:30 molar mixture of diethyl maleate and monoethyl maleate plus a small amount of "light ends", such as ethanol and water, as a bottom product. Distillation can be effected under a reduced pressure of, for example, about 0.5 bar or at an elevated pressure of up to about 5 bar; however, it is conveniently effected at, or just above, atmospheric pressure, e.g. at about 1.05 bar. As it is not necessary to remove all of the "light ends" from the bottom product, the bottom of the first distillation zone can be kept relatively cool thus reducing the risk of thermal decomposition at this stage. The overhead product from the first distillation zone is, as already noted, a mixture of water and ethanol (plus a minor amount of diethyl maleate); preferably the monoethyl maleate:ethanol molar ratio of the reactant mixture fed to the intermediate esterification zone is so controlled that the water content of the overhead product from this distillation step is higher than the water/ethanol azeotrope obtained upon distillation of water/ethanol mixtures at the pressure of distillation. This mixture can then be redistilled in a second distillation zone, again conveniently at or just above atmospheric pressure, to yield a "wet" ethanol overhead product which is drier than the feed to the second distillation zone but is still wetter than the water/ethanol azeotrope obtainable upon distillation of water/ethanol mixtures at the pressure of the second distillation zone. The "wet" ethanol overhead product from the second distillation zone typically contains about 15 mole % of water. Part of this "wet" ethanol overhead product from the second distillation zone can be recycled to the intermediate esterification zone while part is returned to the second distillation zone as a reflux stream, and the remainder is passed to an ethanol dehydration unit to produce "dry" ethanol to form the vaporous feed stream in the secondary esterification zone, if there is only one such zone, or to the final secondary esterification zone, if there is more than one such zone. The bottom product from the second distillation zone is mainly water but contains any diethyl maleate that distils from the first distillation zone.

The ethanol dehydration unit may be of any suitable design capable of producing from a "wet" ethanol stream containing up to about 20 mole % water a sufficient stream of "dry" ethanol with a water content less than about 1 mole % for use as the source of the vaporous feed stream in the secondary esterification zone. Membrane separation techniques can be used for the production of "dry" ethanol; alternatively molecular sieves can be used.

In one preferred form of the process a single secondary esterification zone is used which may comprise a stirred tank reactor containing a charge of a macroreticular ion exchange resin containing sulphonic acid groups, such as Amberlyst 16, through which ethanol vapour is bubbled.

In a further preferred process the secondary esterification zone comprises a reactor containing an immobilised charge of a macroreticular ion exchange resin containing sulphonic acid groups, such as Amberlyst 16, through which ethanol vapour, preferably "dry" ethanol, is passed in countercurrent to a liquid phase containing monoethyl maleate flowing down through the charge of ion exchange resin; in such a process the reactor is operated as a flooded bubble reactor.

In a further preferred process a plurality of secondary esterification zones connected in series are used, each comprising a reactor containing as catalyst a charge of an ion exchange resin containing sulphonic acid groups and/or carboxylic acid groups, such as Amberlyst 16. Although such a process can involve use of only two such reactors, or five or more, there are conveniently used three or four such reactors in series. Each reactor is provided with a suitable screen to retain its respective charge of resin beads in the reactor. The monoethyl maleate feed stream (e.g. an approximately 70:30 molar ratio diethyl maleate:monoethyl maleate mixture) is fed through the reactors in turn in countercurrent flow to a stream of ethanol vapour. "Dry" ethanol is passed through the last reactor in the series, the vaporous effluent from which is then passed through the penultimate reactor, while the vaporous effluent from the penultimate reactor is passed through the ante-penultimate reactor (and so on, if more than three reactors are used). In this way substantially all of the water of esterification produced in each reactor is removed in the vaporous ethanol stream. The liquid phase encounters progressively drier ethanol vapour as it passes from one reactor to the next.

In a modification of this second preferred process the vaporous effluent stream from the final reactor is condensed prior to introduction into the penultimate reactor, while the vaporous effluent stream from the penultimate reactor is also condensed prior to introduction to the ante-penultimate reactor (and so on, if more than three reactors are used). In this form of the process the second stream is supplied in liquid form to all the reactors, except the final reactor, and is vaporised in the respective reactor to form the vaporous stream.

In yet another modification of this process the vaporous effluent stream from the final reactor is compressed prior to introduction into the penultimate reactor, while the vaporous effluent stream from the penultimate reactor is also compressed prior to introduction to the ante-penultimate reactor (and so on, if more than three reactors are used).

The reaction conditions in the or each secondary esterification zone preferably include use of a temperature in the range of from about 100 to about 125° C. and a pressure of from about 1 to about 3 bar. The residence time in the or each secondary esterification zone is typically in the range from about 2 to about 10 hours.

As mentioned above, the bottom product from the second distillation zone contains diethyl maleate in addition to water. Conveniently this mixture is allowed to settle out in a decanter. The aqueous layer can either be discarded or, if an aqueous neutralisation stage is used for final product purification, this aqueous phase can be used to provide the make up water for this aqueous neutralisation stage. The organic layer can be returned to the plant, conveniently upstream from the secondary esterification zone of the process of the invention.

In order that the invention may be clearly understood and readily carried into effect six preferred forms of plant for the continuous production of diethyl maleate, each using a preferred process according to the invention, will now be described, by way of example only, with reference to the accompanying drawings, FIGS. 1 to 6 of which are each a flow diagram of a corresponding plant.

It will be appreciated by those skilled in the art that, since the drawings are diagrammatic, some conventional items of equipment such as heat exchangers, pumps, filters, valves, vacuum equipment, temperature sensors, pressure controllers, and the like, have been omitted from the drawings for the sake of simplicity. It will be readily apparent to the skilled reader that such additional items of equipment may be necessary for the successful operation of the illustrated plants, and the provision and positioning of such ancillary items of equipment form no part of the present invention and will be provided in accordance with standard chemical engineering practice.

Referring to FIG. 1 of the drawings, a continuously operable plant for the production of diethyl maleate is supplied in line 1 with liquid maleic anhydride and in line 2 with ethanol in a mole ratio of about 1:2. The liquid maleic anhydride may contain a minor amount of maleic acid, typically not more than about 5 mole % of maleic acid, and a lower amount, typically less than about 1 mole %, of fumaric acid. Ethanol supplied in line 2 may contain a small amount of water, e.g. about 3.5 mole % of water. This ethanol comprises a mixture of make up ethanol and wet ethanol recycled from an ester hydrogenation plant (not shown) which operates according to the teachings of EP-A-No. 0143634, of WO-A-No. 86/03189 or of WO-A-No. 86/07358 and produces a mixture of butane-1,4-diol, gamma-butyrolactone and tetrahydrofuran. The two streams are mixed in monoesterification reactor 3 by means of stirrer 4. The reaction mixture is held in reactor 3 for a residence time of about 60 minutes, the temperature in reactor 3 being maintained at 95° C.

Essentially quantitative formation of monoethyl maleate occurs in monoesterification reactor 3. A liquid reaction mixture is discharged from reactor 3 in line 5 which contains an approximately equimolar mixture of monoethyl maleate and ethanol, plus a small amount of water.

This mixture is admixed with a further mole of ethanol, supplied as a "wet" ethanol stream containing about 15 mole % of water in line 6. The resulting mixture contains monoethyl maleate, ethanol and water in a mole ratio of about 1:2:0.25 and is then fed into a primary esterification reactor 7 which contains a bed of an ion exchange resin containing —$SO_3H$ groups, such as Amberlyst 16. (The word "Amberlyst" is a Registered Trade Mark). It is maintained at 115° C. under pressure.

The liquid hourly space velocity through the resin bed of primary esterification reactor 7 is approximately 1.75 $hr^{-1}$. About 70 mole % of the monoethyl maleate is esterified to diethyl maleate in passage through reactor 7. The liquid effluent stream in line 8 accordingly contains diethyl maleate, monoethyl maleate, water, and excess ethanol in a molar ratio of approximately 0.7:0.3:0.95:1.3, and possibly also minor amounts of maleic anhydride, maleic acid, fumaric acid, monoethyl fumarate and diethyl fumarate.

This mixture is passed by way of line 8 to a first distillation column 9 which operates at substantially atmospheric pressure. An ethanol/water mixture, in a molar ratio of about 2:1.25, which contains also a minor amount of diethyl maleate, is recovered overhead in line 10 and is fed into a second distillation column 11, also operating at substantially atmospheric pressure. The overhead product in line 10 is a mixture that is wetter than the ethanol/water azeotrope which could be obtained at the pressure of operation of column 9, i.e. substantially atmospheric pressure. Column 11 effects separation of the components of the overhead mixture from column 9 into a bottom product containing water and any diethyl maleate, which bottom product is recovered in line 12, and an ethanol/water overhead product, which is recovered in line 13, that contains about 15 mole % water. Reference numeral 14 indicates a reboiler for column 11 which is fed with steam in line 15.

Part of the ethanol/water mixture in line 13 is condensed in condenser 16 against cooling water supplied in line 17; a proportion of the resulting condensate which is collected in drum 18 is returned to column 11 by way of lines 19 and 20, whilst the remainder is recycled to reactor 7 by way of lines 19 and 6.

The contents of drum 18 can be blanketed with nitrogen supplied in line 21, whilst a vent line 22 is provided to vent non-condensible materials from the plant.

The bottom product from column 9 in line 23 is a mixture of diethyl maleate, monoethyl maleate, and minor amounts of "lights" (e.g. water and ethanol), in a mole ratio of approximately 0.7:0.3:0.2. Part of this mixture is recycled to column 9 by way of line 24 and reboiler 25 whose steam heating line is indicated at 26, and the remainder is passed through lines 27 and 28 to the top end of a secondary esterification reactor 29 containing a charge of a macroreticular ion exchange resin containing —SO$_3$H groups, such as Amberlyst 16. In order to immobilise the resin within the reactor 29 it is preferably loaded into the reactor as small packages wrapped in wire mesh, each containing a small quantity of beads of the resin. The reactor may include a number of internal trays (not shown) each carrying a layer of the resin, whether in the form of wrapped packages or in the form of free resin beads. "Dry" ethanol vapour is introduced by means of line 30 into the bottom end of reactor 29 and is maintained in the vapour phase by contact with the downflowing hot liquid mixture from line 28. Further esterification occurs in secondary esterification reactor 29 by reaction of residual monoethyl maleate in the downflowing liquid mixture with ethanol. Water produced in the esterification reaction is stripped by the upflowing ethanol vapour and the resulting "wet" ethanol vapour is fed by way of line 31 to an intermediate part of first distillation column 9. The liquid product stream, which now contains a minor amount only of monoester, i.e. monoethyl maleate and possibly also monoethyl fumarate, and mainly comprises diester, i.e. diethyl maleate and possibly also diethyl fumarate, besides traces of ethanol and water, exits reactor 29 in line 32.

Typical reaction conditions in reactor 29 include use of a temperature of about 115° C. and a pressure of about 2 bar. The residence time in secondary esterification reactor 29 is at least 4 hours.

"Dry" ethanol for supply in line 30 is provided by means of a suitable ethanol dehydration unit 33. This can utilise a membrane to separate "dry" ethanol from the wet ethanol fed thereto in line 34; alternatively it can utilise a molecular sieve to achieve the same end. The feed stream to dehydration unit 33 is supplied by way of line 35 and compressor 36 from the overhead stream in line 13 from second distillation column 11. Water is recovered from ethanol dehydration unit 33 in the form of a "wet" ethanol stream which is recycled in line 37 from dehydration unit 33 to an intermediate part of second distillation column 11. Typically the "dry" ethanol in line 30 has a water content of less than 2 mole %, e.g. about 1.5 mole % or less.

Part of the mixture of water and diethyl maleate which is recovered as a bottom product from second distillation column 11 in line 12 is fed in line 38 to a decanter 39 in which it settles out to form two phases. The water-rich upper layer is rejected as effluent or is supplied in line 40 for use as make-up water to a downstream aqueous neutralisation stage, described in more detail hereafter, if such is included in the plant. The lower layer in decanter 39, which consists mainly of diethyl maleate, is passed in line 41 for admixture with the liquid stream in line 27 and subsequent treatment in reactor 29. Reference numeral 42 indicates a vent line from decanter 39 connected to an intermediate part of column 11.

The liquid product stream from reactor 29 in line 32 is passed to a third distillation column 43 which is operated under vacuum (0.8 bar). Ethanol and any water present are recovered overhead in line 44 and condensed in condenser 45 whose chilled water supply line is indicated at 46. The resulting condensate is collected in drum 47. Reference numeral 48 indicates a connection to a vacuum pump or steam ejector (not shown). Part of the condensate from drum 47 is recycled to the top of column 43 in line 49 to form a reflux stream, whilst the remainder is returned to an upper part of reactor 29 in line 50.

The bottom product from third distillation column 43 is recovered by way of line 51 and consists essentially of diester, i.e. diethyl maleate or a mixture of diethyl maleate with a minor amount of diethyl fumarate, and contains a small amount only, e.g. about 2 mole % or less, of monoethyl maleate and other minor impurities including maleic acid, monoethyl fumarate, and fumaric acid. The content of monoethyl maleate depends on the water content in the ethanol vapour stream in line 30; the lower the water content in this ethanol vapour stream is, the lower is the monoethyl maleate content of the diethyl maleate product stream in line 51.

Part of the stream in line 51 is recycled to column 43 by way of line 52 and a reboiler 53 which is fed with steam in line 54.

The diester stream in line 51 can be used for some purposes without further purification. However, it will often be preferred to purify this by removing the final traces of monoester therefrom. This can be achieved by washing with aqueous alkali, e.g. aqueous sodium carbonate, possibly followed by a subsequent water wash, in neutralisation stage 55. Make up water for washing can be supplied to neutralisation stage 55 in line 40 whilst solid sodium carbonate or sodium carbonate solution is supplied as necessary as indicated at 56. A small amount of alkaline waste aqueous wash liquor containing a minor amount of the sodium salt of monoethyl maleate is discarded in line 57.

The washed diester is then fed in line 58 to a further distillation column 59 operated at 0.75 bar. Water is recovered overhead in line 60 and is condensed in condenser 61 whose cooling water supply line is indicated at 62. A part of the condensate is recycled from drum 63 to neutralisation stage 55 by way of lines 64 and 65, the remainder being returned to column 59 as a reflux stream in line 66. Reference numeral 67 represents a connection to a vacuum pump or steam ejector (not shown).

Part of the diester bottom product from column 59 in line 68 is fed in line 69 to a reboiler 70 fed with steam in line 71 for recycle to column 59. The remainder is fed in line 72 to a final purification column 73 in which it is redistilled at a pressure of 0.6 bar. The overhead product in line 74 is condensed in condenser 75 against cooling water in line 76; part of the condensate from drum 77 is removed in line 78 as pure diester. Such diester is predominantly diethyl maleate but contains also a minor amount of diethyl fumarate resulting either from isomerisation in the course of esterification reactions or as a result of the fact that the maleic anhydride supplied in line 1 contains a minor amount of fumaric acid. The remainder of the condensate is returned from drum 77 to column 73 as a reflux stream in line 79. A connection to a vacuum pump or steam ejector (not shown) is indicated at 80. A reboiler 81 fed by lines 82 and 83 is provided for column 73; this reboiler is supplied with steam in line 84. Any build up of "heavies" is controlled by taking a purge stream in line 85.

As described above reactor 29 is operated as a single pass reactor. If desired, part of the liquid product stream from reactor 29 can be recycled to the inlet end of reactor 29 in line 86.

Figure 2:
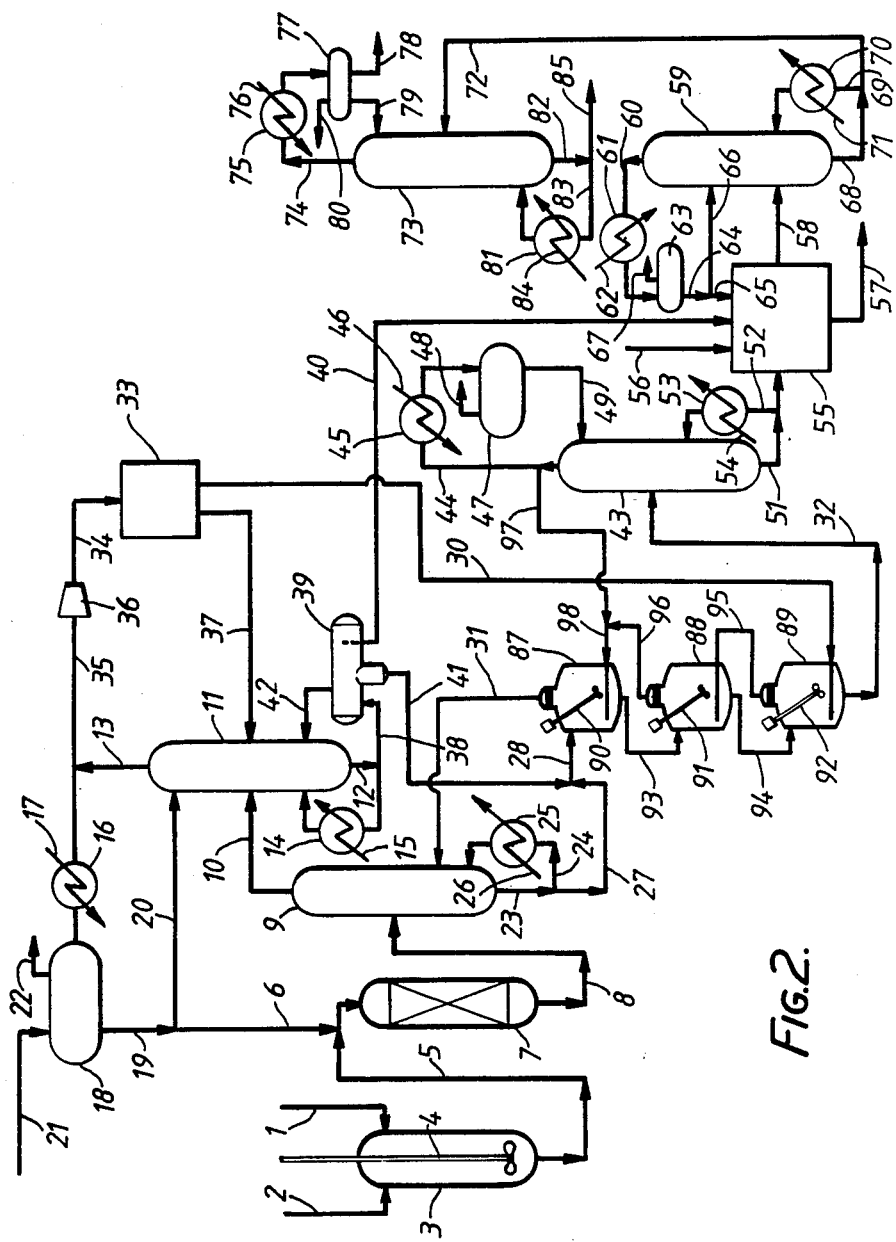

The plant of FIG. 2 is similar to that of FIG. 1 and like reference numerals have been used in both Figures to indicate like parts. However, the single stage secondary esterification reactor 29 of the plant of FIG. 1 is replaced in the plant of FIG. 2 by a series of continuously stirred tank reactors 87, 88 and 89, each containing a charge of Amberlyst 16 ion exchange resin beads. The stirrers for secondary esterification reactors 87, 88 and 89 are indicated at 90, 91 and 92. Typical reaction conditions in each of reactors 87, 88 and 89 are similar to those mentioned for reactor 29 of the plant of FIG. 1. Liquid phase is led from the first of the stirred reactors 87 to the second reactor 88 in the series by way of line 93, whilst liquid is fed from reactor 88 to the third of the series, i.e. reactor 89, in line 94. "Dry" ethanol vapour in line 30 is fed to the bottom of reactor 89. A mixture of ethanol vapour and water vapour resulting from the esterification occurring in reactor 89 exits the top of reactor 89 in line 95 and is fed to the bottom of reactor 88, in which it picks up further water vapour. The resulting ethanol/water vapour mixture exits the top of reactor 88 in line 96, is admixed with recycled ethanol vapour in line 97 from line 44 and is fed to the bottom of reactor 87 in line 98. The vaporous effluent from reactor 87 is a wet ethanol vapour and is passed by way of line 31 to distillation column 9.

The liquid feed to reactor 87 is an approximately 70:30 molar ratio diethyl maleate:monoethyl maleate mixture; in line 93 the corresponding molar ratio is about 85:15, while in line 94 it is about 92:8. The corresponding mixture in line 32 is an approximately 99:1 molar mixture of diethyl and monoethyl maleates. The precise values of these ratios will depend, inter alia, upon the water content and rate of supply of the "dry" ethanol supplied in line 30, and upon the temperature and residence time of the liquid reaction mixture in each of reactors 87, 88 and 89.

Figure 3:
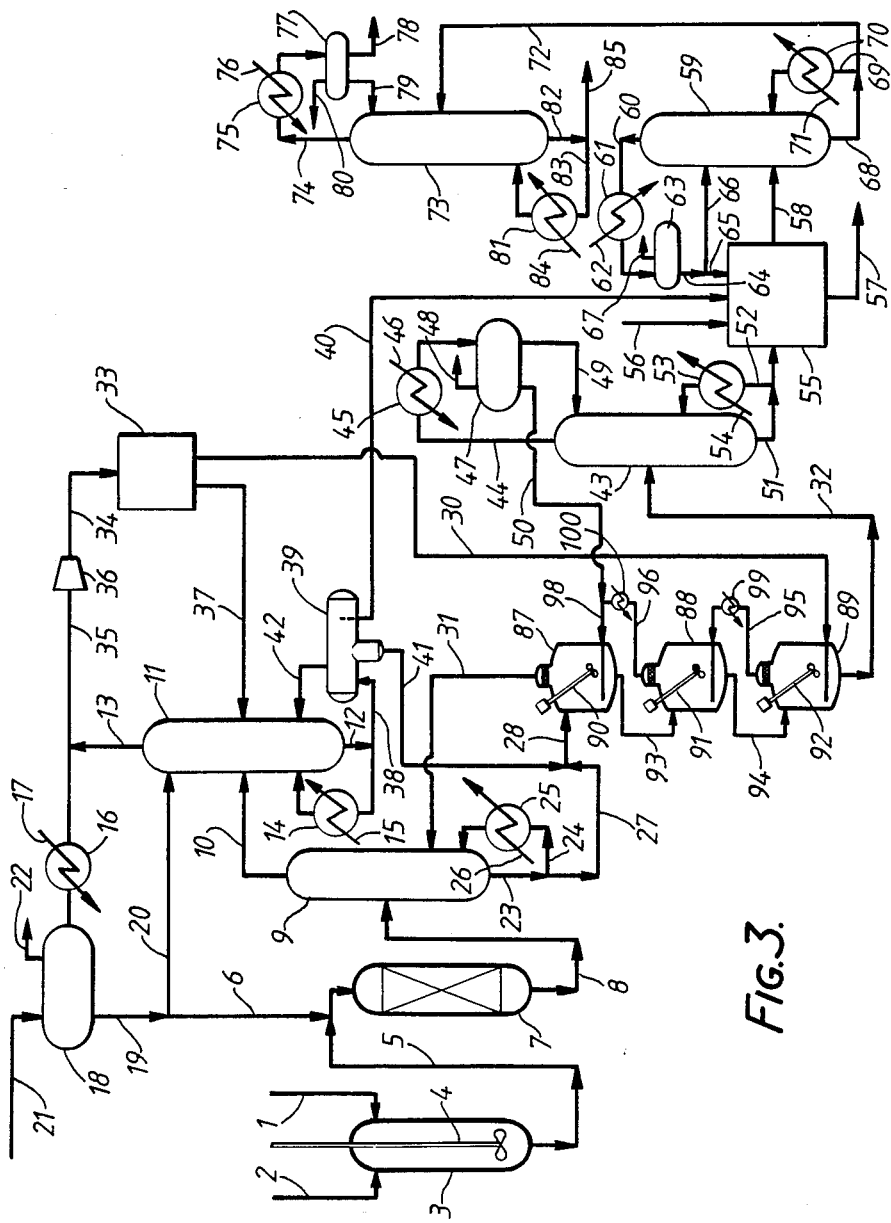

The plant of FIG. 3 is generally similar to that of FIG. 2, except that condensers 99 and 100 are provided in lines 95 and 96 respectively and that the condensate from condenser 100 is admixed with condensate in line 50 for supply to line 98. Thus ethanol is fed as a liquid to each of reactors 88 and 87 and is vaporised therein by contact, with the downflowing hot ester-containing liquid stream.

Figure 4:
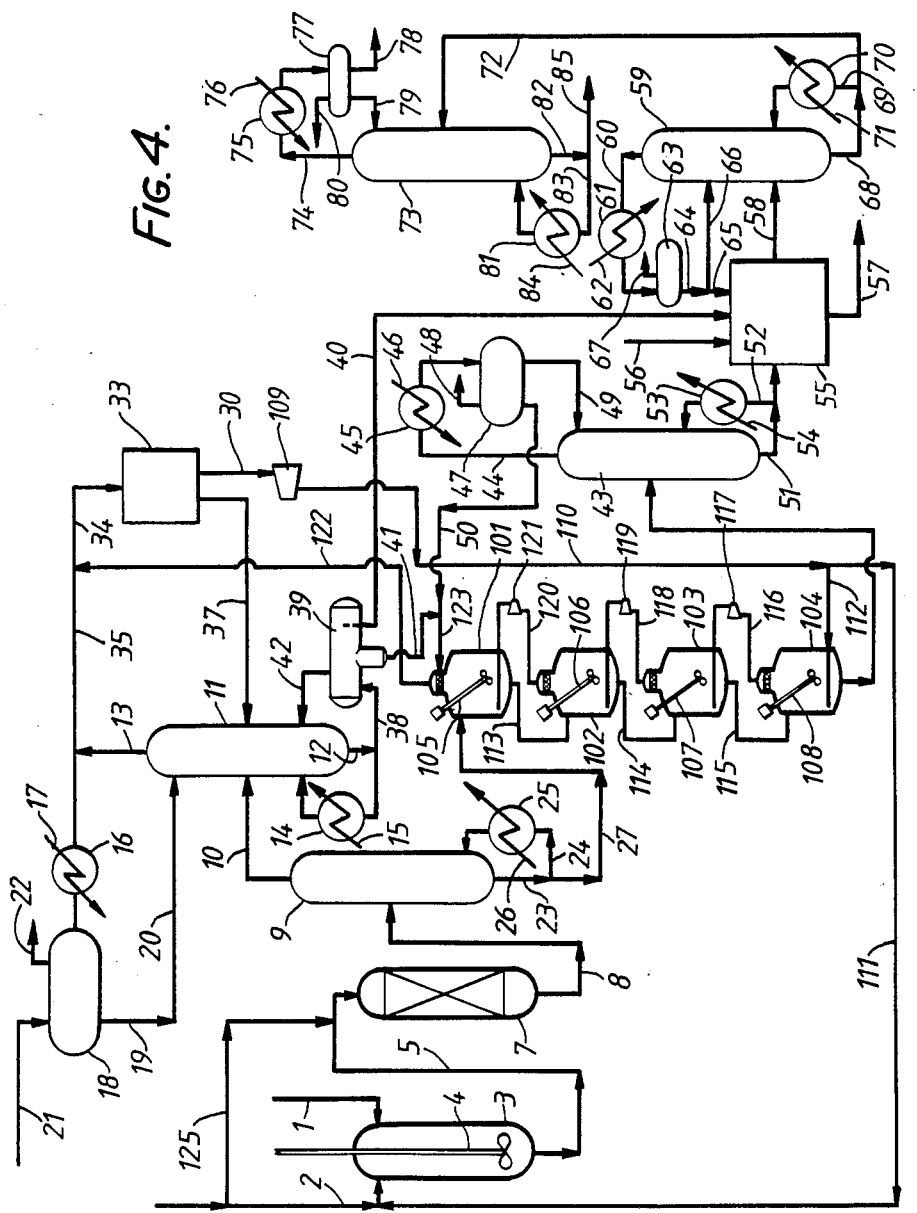

In the plant of FIG. 4 the single secondary esterification reactor 29 of FIG. 1 is replaced by four stirred tank reactors 101, 102, 103 and 104 connected in series; each of these reactors contains a charge of Amberlyst 16. Reference numerals 105, 106, 107 and 108 indicate their respective stirrers "Dry" ethanol vapour is fed from ethanol dehydration unit 33 in line 30 under the influence of compressor 109 (which replaces compressor 36 of the plant of FIG. 1). The compressed vapour passes on in line 110, a part being condensed and fed to mono-esterification reactor 3 by way of line 111, whilst the remainder is fed by way of line 112 to a sparger fitted at the lower end of the fourth reactor 104.

The bottom product from column 9 is fed by way of lines 23 and 27 to the top of the first reactor 101. A liquid stream is taken from the bottom of reactor 101 in line 113 and is passed to the top of reactor 102. In a similar manner line 114 feeds liquid from the bottom of reactor 102 to the top of reactor 103, whilst liquid is taken from reactor 103 to reactor 104 in line 115.

Ethanol vapour containing water of esterification from reactor 104 entrained therein is fed by means of line 116 and blower 117 to a sparger in the bottom of reactor 103. In similar manner line 118 and blower 119 are used to pass ethanol vapour and entrained water vapour to a sparger in the bottom of reactor 102. The vapours exiting reactor 102 are fed by means of lines 120 and blower 121 to a sparger in the bottom of reactor 101.

Wet ethanol vapour is recovered from the top of reactor 101 in line 122 and is combined with the vapours in line 35 to form a combined stream which is fed in line 34 to ethanol dehydration unit 33.

The ethanol recycle stream in line 50 and ester stream from decanter 39 in line 41 are combined and fed to the top of reactor 101 in line 123.

Instead of recycling "wet" ethanol from line 19 by way of line 6 to line 5, as occurs in the plant of FIG. 1, a corresponding amount of make up ethanol is supplied to line 5 from line 2 by way of line 125.

In each of the plants illustrated in FIGS. 1 to 4 it is proposed that the neutralisation stage 55 shall involve use of an aqueous alkali, followed by a subsequent water wash; alternatively neutralisation can be achieved using an aqueous alkaline wash liquor comprising an alkali metal (e.g. sodium) hydroxide, carbonate, bicarbonate, or a mixture of two or more thereof dissolved in an aqueous solution of the corresponding di-(alkali metal) salt of maleic acid (e.g. disodium maleate), followed by distillation in column 59.

Figure 5:
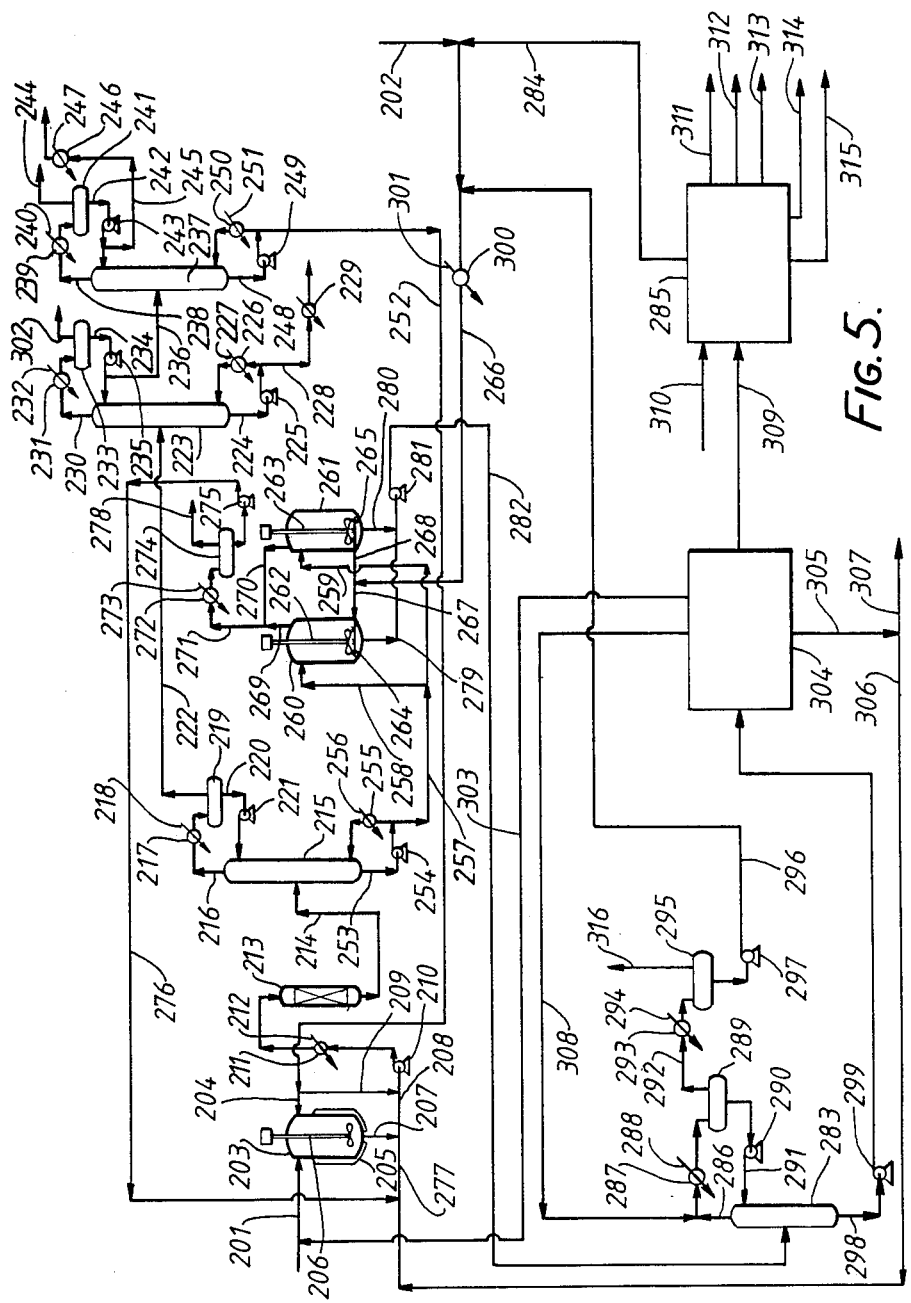

Alternatively the neutralisation stage 55 of each of the plants illustrated in FIGS. 1 to 4 can be replaced by a purification stage FIG. 5 of the drawings illustrates a continuously operable plant for production of diethyl maleate which is then used for the co-production of butane-1,4-diol, gamma-butyrolactone and tetrahydrofuran. This plant is supplied in line 201 with liquid maleic anhydride and in line 202 with make up ethanol. A mixture of maleic anhydride and ethanol is supplied to a monoesterification reactor 203 which is also supplied with a wet ethanol stream in line 204 in an ethanol:maleic anhydride molar ratio of about 2:1. The ethanol supplied in line 204 contains about 15 to 20 mole % of water. Reactor 203 is fitted with a jacket 205 by means of which it can be cooled, as necessary, by admission of cooling water thereto. The contents of monoesterification reactor can be mixed by means of stirrer 206. The reaction mixture is held in reactor 203 for a residence time of about 60 minutes, the temperature in reactor 203 being maintained at about 100° C.

Essentially quantitative formation of monoethyl maleate occurs in monoesterification reactor 203. A liquid reaction mixture is discharged from reactor 203 in line 207 which contains an approximately equimolar mixture of monoethyl maleate and ethanol, plus a corresponding amount of water.

This mixture is passed forward in line 208 and is admixed with a further mole of ethanol, supplied as a "wet" ethanol stream containing about 15 to 20 mole % of water in line 209. The resulting mixture contains monoethyl maleate, ethanol and water in a mole ratio of about 1:2:0.25 and is then pumped by means of pump 210 through heater 211, which is supplied with steam in line 212, to a primary esterification reactor 213 which contains a bed of an ion exchange resin containing $-SO_3H$ groups, such as Amberlyst 16. (The word "Amberlyst" is a Registered Trade Mark). It is maintained at about 105° C. under pressure.

The liquid hourly space velocity through the resin bed of primary esterification reactor 213 is approximately 1.75 $hr^{-1}$. About 70 mole % of the monoethyl maleate is esterified to diethyl maleate in passage through reactor 213. The liquid effluent stream in line 214 accordingly contains diethyl maleate, monoethyl maleate, water, and excess ethanol in a molar ratio of approximately 0.7:0.3:0.95:1.3, and possibly also minor amounts of maleic anhydride, maleic acid, fumaric acid, monoethyl fumarate and diethyl fumarate.

This mixture is passed by way of line 214 to a first distillation column 215 which operates at substantially atmospheric pressure. An ethanol/water mixture, in a molar ratio of about 2:1.25, which contains also minor amounts of diethyl maleate, of tetrahydrofuran and of diethyl ether, is recovered overhead in line 216.

The overhead product in line 216 is a mixture that is wetter than the ethanol/water azeotrope which could be obtained at the pressure of operation of column 215, i.e. substantially atmospheric pressure. Part of the vapours in line 216 are condensed in condenser 217 which is supplied in line 218 with cooling water. The resulting condensate passes on to condensate drum 219 and is recycled in line 220 by pump 221 to form a reflux stream for column 215. The uncondensed vapours pass on in line 222 to an ethanol recovery column 223, from which a bottom product containing water and any diethyl maleate is recovered in line 224; part of this bottom product is recycled by means of pump 225 through heater 226, whose steam line is indicated at 227, to column 223 whilst the remainder is passed in line 228 to cooler 229 and then to a water treatment section (not shown).

An overhead product is recovered from column 223 in line 230, that contains about 15 to 20 mole % water. It also contains any light boiling materials present such as diethyl ether and tetrahydrofuran.

The ethanol/water mixture in line 230 is condensed in condenser 231 against cooling water supplied in line 232; part of the resulting condensate which is collected in drum 233 is returned to column 223 by way of line 234 and pump 235 to form a reflux stream for column 223. Reference numeral 302 indicates a vent line for drum 233.

The rest of the condensate from drum 233 is passed in line 236 to an ether recovery column 237 from which any diethyl ether and other "lights", e.g. tetrahydrofuran, are recovered overhead in line 238 and are condensed in condenser 239 whose coolant supply line is indicated at 240. Condensate is returned as a reflux stream to column 237 from condensate drum 241 by means of line 242 and pump 243. Vapours are vented to a flare stack in line 244 while diethyl ether is passed to storage in line 245 via cooler 246 which is supplied with chilled water in line 247. Such diethyl ether also contains some of the tetrahydrofuran present in the material in line 222.

The bottom product from column 237 in line 248 is a wet ethanol stream containing about 15 to 20 mole % of water. Part is recycled to column 237 by pump 249 through reboiler 250, which is heated with steam supplied in line 251, whilst the remainder is recycled to monoesterification reactor 203 in lines 252 and 204.

The bottom product from column 215 in line 253 is a mixture of diethyl maleate, monoethyl maleate, and minor amounts of "lights" (e.g. water and ethanol), in a mole ratio of approximately 0.7:0.3:0.2. Part of this mixture is recycled to column 215 by way of pump 254 and reboiler 255 whose steam heating line is indicated at 256, and the remainder is passed through line 257 and then through lines 258 and 259 to the respective top end of a pair of secondary esterification reactors 260, 261, each containing a charge of a macroreticular ion exchange resin containing $-SO_3H$ groups, such as Amberlyst 16.

Each reactor 260, 261 is provided with a stirrer 262, 263 and is fitted at its lower end with a respective vapour distributor 264, 265. Ethanol vapour is introduced by means of lines 266, 267 and 268 through distributors 264, 265 into the bottom ends of reactors 260, 261.

Further esterification occurs in secondary esterification reactors 260, 261 by reaction of residual monoethyl maleate with ethanol. Water produced in the esterification reaction is stripped by the upflowing ethanol vapour and the resulting "wet" ethanol vapour in lines 269 and 270 is fed by way of line 271 through condenser 272, which is supplied with cooling water in line 273, to drum 274 from which it is recycled by pump 275 and lines 276, 277 and 208 to primary esterification reactor 213.

Reference numeral 278 indicates a vent line.

The liquid product stream from secondary esterification reactors 260, 261, which now contains diethyl maleate and monoethyl maleate in a molar ratio of about 85:15, besides minor amounts of ethanol and water, exits reactors 260, 261 in lines 279 and 280 and is pumped by means of pump 281 through line 282 to a flash column 283 which will be described further below.

Typical reaction conditions in reactors 260, 261 include use of a temperature of about 115° C. and a pressure of about 1 bar. The residence time in secondary esterification reactors 260, 261 is about 2½ hours.

The ethanol vapour supplied in line 266 is a mixture of make up ethanol from line 202 and ethanol recycled in line 284 from the product recovery section of a hydrogenation plant 285 (described further below); this ethanol mixture is vaporised in heater 300 which is supplied with steam in line 301.

The liquid product stream from reactors 260, 261 in line 282 is passed to a column 283 which is operated under vacuum (about 0.1 bar). Ethanol and any water present are recovered overhead in line 286 and part of this overhead stream is condensed in condenser 287 which is cooled to about 70° C. by tempered water supplied in line 288. The resulting condensate is collected in drum 289. The condensate from drum 289 is recycled to the top of column 283 by pump 290 in line 291 to form a reflux stream. The uncondensed part of the stream from line 286, which consists mainly of ethanol and water, passes on in line 292 and is condensed in a further condenser 293 whose chilled water supply line is indicated at 294. The resulting condensate is collected in drum 295 and is recycled to the secondary esterification reactors 260, 261 by means of line 296 and pump 297. Reference numeral 316 indicates a connection to a vacuum pump (not shown).

The bottom product from column 283 is recovered by way of line 298 and consists essentially of a mixture of diethyl maleate and monoethyl maleate, besides other minor impurities including maleic acid, diethyl fumarate, monoethyl fumarate, and fumaric acid.

The ester stream in line 298 is pumped by a pump 299 to a purification plant 304. This purification plant 304 may further include a distillation section for separation of diethyl maleate from diethyl fumarate. A recycle stream containing a mixture of diethyl maleate and monoethyl maleate is returned from purification plant 304 by way of lines 305 and 306. A purge stream is taken in line 307. A condensate containing maleic anhydride is recycled to monoesterification reactor 203 in line 303. A mixture consisting mainly of ethanol and water is recycled to column 283 in line 308.

Acid free diethyl maleate, possibly containing a minor amount of diethyl fumarate, is recovered from purification plant 304 in line 309 and is passed to a vapour phase hydrogenation plant 285 which is arranged to operate according to the process described in EP-A-No. 0143634, in WO-A-No. 86/03189 or in WO-A-No. 86/07358. Plant 205 is supplied with hydrogen in line 310. Such a plant includes a product recovery section.

There are recovered from hydrogenation plant 285 a stream of tetrahydrofuran in line 311, a stream of gamma-butyrolactone in line 312, and a stream of butane-1,4-diol in line 313. Minor amounts of n-butanol and of "heavies" are recovered in lines 314 and 315 respectively.

Figure 6:
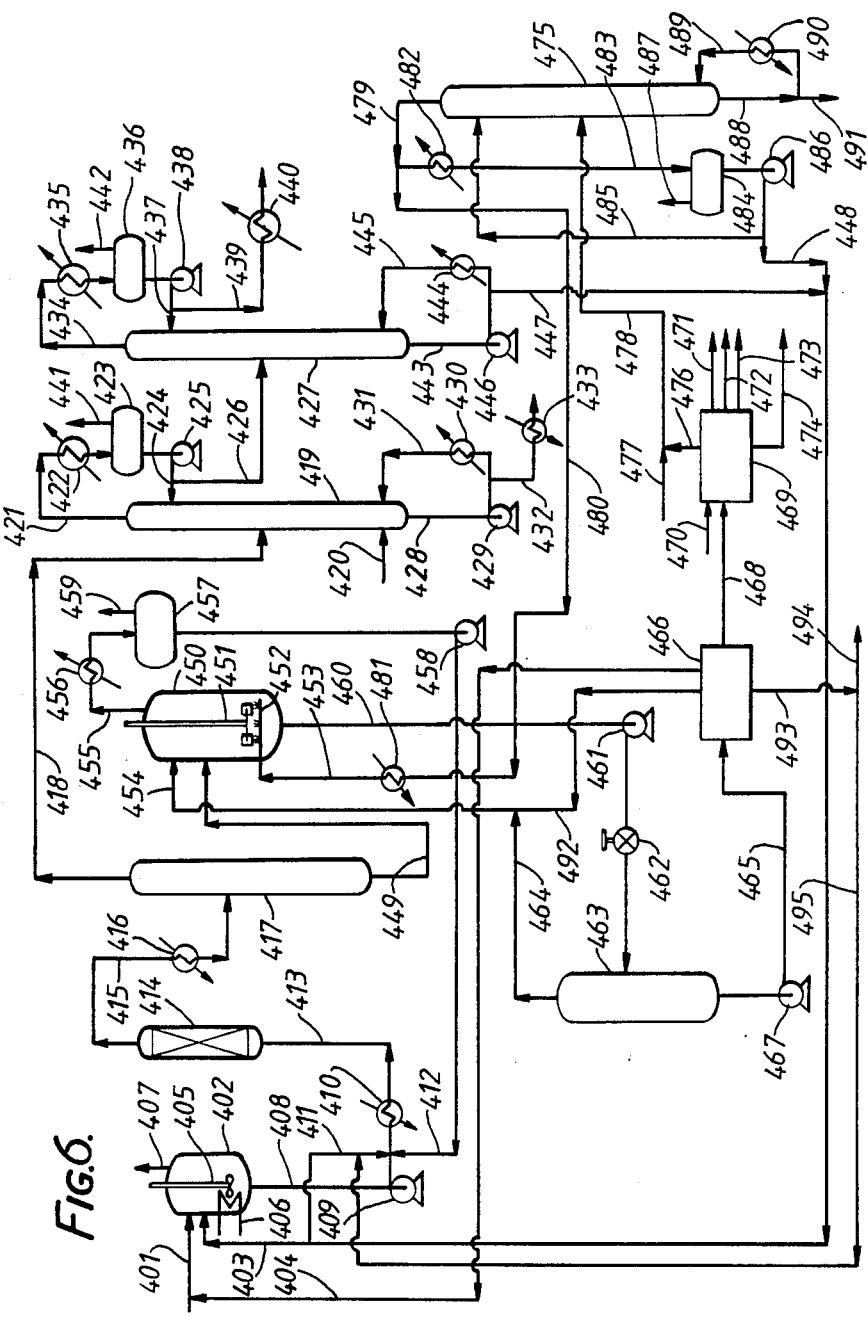

In the plant of FIG. 6 maleic anhydride is supplied in line 401 to monoesterification reactor 402, to which is also supplied a stream containing ethanol in line 403. Reactor 402 is also fed by way of line 401 with a recycle stream from line 404 that contains recovered maleic anhydride and diethyl maleate. Monoesterification reactor 402 is provided with a stirrer 405, with a cooling coil 406 (which doubles as a steam heating coil at start up of the plant), and with a vent line 407. Maleic anhydride reacts with ethanol in reactor 402 to produce monoethyl maleate in the absence of a catalyst. The liquid reaction mixture from reactor 402 is discharged in line 408 and pumped by pump 409 to steam heater 410. Upstream from heater 410 it is admixed with two streams comprising further ethanol supplied in lines 411 and 412. The mixed stream flows on in line 413 to a primary esterification reactor 414 which contains a fixed bed of an acidic ion exchange resin, such as Amberlyst 16. Reaction between monoethyl maleate and ethanol to form diethyl maleate takes place in reactor 414.

An intermediate esterification product mixture is recovered from primary esterification reactor 414 in line 415 and is heated by means of steam heater 416 before entering a flash distillation column 417. A vaporous stream containing mainly ethanol and water, but also a minor amount of diethyl ether (besides tetrahydrofuran and a trace of diethyl maleate, both of which are present in a recycle stream to monoesterification reactor 402 as described further below), is recovered overhead in line 418 which leads to an ethanol recovery column 419. This is also supplied with water in line 420 which has been used in condensers in the plant and which includes water containing streams recovered from elsewhere in the plant. The overhead product from column 419 in line 421 is condensed by means of condenser 422 and contains mainly ethanol with lesser amounts of water, diethyl ether and tetrahydrofuran. The resulting condensate collects in drum 423; part is returned to column 418 in line 424 by pump 425 to form a reflux stream, whilst the remainder is passed in line 426 to an ether recovery column 427. A part of the bottom product from column 419 in line 428 is recycled by pump 429 to column 419 through column reboiler 430 and line 431. This bottom product in line 428 is mainly water but contains some ethanol and diethyl maleate. The remainder of the bottom product in line 428 is taken in line 432, cooled in cooler 433 and passed on to a water treatment plant (not shown).

From the ether recovery column 427 is recovered overhead in line 434 a vaporous stream comprising diethyl ether, together with minor amounts of ethanol, water and tetrahydrofuran. This is condensed by means of condenser 435. The resulting condensate collects in drum 436; part is recycled as a reflux stream to column 427 in line 437 by pump 438, while the remainder is passed in line 439 to cooler 440 and thence to storage.

Reference numerals 441 and 442 represent vent lines for condensate drums 423 and 436 respectively.

The bottom product from ether recovery column 427 in line 443 is mainly ethanol, but contains a minor amount of water and small amounts of tetrahydrofuran and diethyl ether. Part is returned through reboiler 444 in line 445 to column 427 by means of pump 446, whilst the remainder is recycled in line 447 for admixture with further ethyl alcohol in line 448 to form the stream in line 403.

The bottom product from flash distillation column 417 is taken in line 449 to a secondary esterification reactor 450. This is provided with a stirrer 451 and a sparger 452 which is connected to a line 453 through which ethanol vapour is supplied to reactor 450. Further reaction of monoethyl maleate and ethanol occurs in reactor 450, resulting in formation of additional diethyl maleate. A stream containing recycled ethanol is returned to reactor 450 in line 454.

Water of esterification is stripped by the upflowing ethanol vapour which exits reactor 450 in line 455. This vapour is condensed in condenser 456 and collects in drum 457 from which it is recycled to primary esterification reactor 402 in line 412 by pump 458. Reference numeral 459 represents a vent line for drum 457.

A liquid product mixture containing mainly diethyl maleate but also a lesser amount of monoethyl maleate, together with some ethanol and water and traces of diethyl ether and tetrahydrofuran, is recovered in line 460. This is pumped by pump 461 through a pressure reduction valve 462 to a flash distillation column 463 which is operated under vacuum. The overhead stream in line 464 is recycled to secondary esterification reactor 450 by way of line 454 and contains ethanol and water besides some diethyl maleate and a trace of monoethyl maleate.

The bottom product from column 463 is pumped in line 465 to a diethyl maleate purification plant 466 by pump 467. It preferably includes a distillation column for separation of diethyl maleate from diethyl fumarate. Acid free diethyl maleate is recovered in line 468 and is passed to a vapour phase hydrogenation plant 469. This is arranged to operate according to the process described in EP-A-No. 0143634, in WO-A-No. 86/03189 or in WO-A-No. 86/07358 and is supplied with hydrogen in line 470. It includes a product recovery section. There are recovered from plant 469 a stream of tetrahydrofuran in line 471, a stream of gamma-butyrolactone in line 472, and a stream of butane-1,4-diol in line 473. Minor amounts of "heavies" are recovered in line 474.

Instead of providing for recovery of n-butanol by-product within the product recovery section of the hydrogenation plant 469, as in the plant of FIG. 5, a column 475 is fed with a mixture of "lights" recovered from plant 469, including ethanol and n-butanol, in line 476 and with make up ethanol in line 477. The mixed stream in line 478 yields upon distillation a vaporous stream in line 479 part of which flows on in line 480 through heater 481 and line 453 to the secondary esterification reactor 450. The rest of the vaporous stream in line 479 passes to a condenser 482. The resulting condensate in line 483 collects in drum 484, part being returned as a reflux stream to column 475 in line 485 by means of pump 486, and the remainder flowing in line 448 to join line 447. Reference numeral 487 indicates a vent line for drum 484. A stream of n-butanol, produced as a by-product in hydrogenation plant 469, is recovered from the bottom of column 475 in line 488. Part of this stream is returned to column 475 in line 489 through reboiler 490. The remainder is passed to storage in line 491.

From diethyl maleate purification plant 466 there is recovered in line 492 a stream containing a mixture of ethanol, diethyl maleate, water, and maleic anhydride, besides traces of tetrahydrofuran, diethyl ether, maleic acid, and fumaric acid. This is admixed with the material in line 464 to form the stream in line 454. Also recovered from diethyl maleate purification plant 466 is a stream containing maleic anhydride and diethyl maleate, besides traces of ethanol and water; this is recycled to monoesterification reactor 402 in line 404. Another stream recovered from plant 466 in line 493 contains a mixture of monoethyl maleate and diethyl maleate and minor amounts of "heavies". Part is purged in line 494, whilst the remainder is recycled to primary esterification reactor 414 in line 495.

The composition of some of the more important streams in the plant of FIG. 6 and some typical operating conditions are set out in the Table. (In the Table "THF" means tetrahydrofuran and "DEE" means diethyl ether; in addition the items "Monoethyl maleate" and "Diethyl maleate" include minor amounts of monoethyl fumarate and of diethyl fumarate respectively).

TABLE

| LINE NO. | 401 | 403 | 404 | 408 | 413 | 415 | 449 | 453 | 454 | 460 |
|---|---|---|---|---|---|---|---|---|---|---|
| Flow rates in kg moles per hour | | | | | | | | | | |
| Ethanol | — | 134.1 | 0.3 | 52.2 | 305.9 | 238.9 | 13.5 | 159.0 | 39.1 | 33.0 |
| Water | — | 25.5 | Trace | 23.5 | 90.5 | 155.8 | 14.3 | 19.6 | 7.1 | 8.9 |
| THF | — | 1.0 | — | 1.0 | 1.7 | 1.7 | Trace | Trace | Trace | Trace |
| DEE | — | 0.5 | — | 0.5 | 1.5 | 2.9 | Trace | 0.2 | Trace | Trace |
| Maleic anhydride | 77.2 | — | 7.0 | — | — | — | — | — | 1.6 | — |
| Maleic acid | — | — | Trace | 12.5 | 12.5 | — | — | — | Trace | — |
| Fumaric acid | — | — | — | 0.1 | 0.1 | — | — | — | — | — |
| Monoethyl maleate | — | — | — | 61.1 | 73.5 | 35.0 | 35.0 | — | Trace | 20.9 |
| Diethyl maleate | — | — | 2.7 | 13.2 | 30.6 | 81.6 | 81.5 | — | 5.6 | 99.1 |
| "Heavies" | — | — | — | — | 1.4 | 1.7 | 1.7 | — | — | 1.9 |
| Temperature (°C.) | 60 | 40 | 91 | 90 | 100 | 119 | 157 | 108 | 10 | 115 |
| Pressure (bar) | 6.0 | 6.0 | 6.0 | | 6.5 | 5.0 | 1.8 | 1.8 | 1.1 | 1.1 |

It will be readily apparent to the skilled reader that the illustrated forms of plant can readily be modified to operate using other $C_1$ to $C_4$ alkyl alcohols to produce di-($C_1$ to $C_4$ alkyl) maleates other than diethyl maleate. For example, in the case of the plants of FIGS. 1 to 4, as methanol does not form an azeotrope with water, separation of water from the overhead product in line 10 can be effected by distillation and no separate dehydration unit 33 is required to produce a sufficiently "dry" methanol stream for supply in line 25.

When operating with n-propanol to produce di-n-propyl maleate little or no modification of the illustrated plants will be required as n-propanol forms single phase azeotropes with water in much the same way as ethanol.

n-butanol also forms an azeotrope with water but this separates into two layers upon cooling. Hence, in the case of the plants of FIGS. 1 to 4, decantation can be used to form a "dry" n-butanol stream in line 30 for production of di-n-butyl maleate.

What is claimed is:

1. A process for the production of a dialkyl maleate which comprises supplying a first liquid feed comprising a monoalkyl maleate to an esterification zone containing a charge of a solid esterification catalyst, supplying a second feed stream comprising an alkyl alcohol to said esterification zone at an elevated temperature sufficient to form or maintain therein a vaporous stream containing said alkyl alcohol, intimately contacting said first liquid feed in said esterification zone in the presence of said catalyst with said vaporous stream, recovering from said esterification zone a vaporous effluent stream containing in addition to alkyl alcohol vapor, also water in vapor form, said water being produced in said esterification zone by esterification of said monoalkyl maleate with said alkyl alcohol, and recovering from said esterification zone a liquid product containing dialkyl maleate.

2. A process according to claim 1, in which said first liquid feed is continuously supplied to said esterification zone and in which said liquid product is continuously recovered therefrom.

3. A process according to claim 1, in which said second feed stream is supplied to said esterification zone in vapour form.

4. A process according to claim 1, in which said second feed stream is supplied to said esterification zone in liquid form.

5. A process according to claim 1, in which said esterification zone comprises a reactor containing a charge of an immobilised ion exchange resin containing acidic groups selected from the group consisting of sulphonic acid groups and carboxylic acid groups.

6. A process according to claim 5, in which said immobilised ion exchange resin comprises packages wrapped in wire mesh, each containing a quantity of beads of said resin.

7. A process according to claim 1, in which said vaporous stream is caused to pass through said esterification zone in countercurrent to said first liquid.

8. A process according to claim 5, in which the water content of said second feed stream is less than about 1 mole %.

9. A process according to claim 1, in which said esterification zone comprises a stirred tank reactor containing a charge of an ion exchange, resin containing acidic groups selected from the group consisting of sulphonic acid groups and carboxylic acid groups.

10. A process according to claim 9, in which the water content of said second feed stream is less than about 15 mole %.

11. A process according to claim 1, in which a plurality of said esterification zones connected in series are used, each said esterification zone comprising a reactor containing a charge of an ion exchange resin containing acidic groups selected from the group consisting of sulphonic acid groups and carboxylic acid groups.

12. A process according to claim 11, in which at least one of said reactors is a stirred tank reactor.

13. A process according to claim 11, in which the water content of the second feed stream supplied to the final one of said esterification zones is lower than the corresponding water content of the respective second feed stream supplied to any preceding one of said plurality of esterification zones.

14. A process according to claim 13, in which the water content of the second feed stream to said final esterification zone is less than about 1 mole %.

15. A process according to claim 11, in which the water content of the respective second feed stream supplied to each of said plurality of esterification zone decreases progressively from one zone to the next in the series.

16. A process according to claim 11, in which the second feed stream to the, or to each, said esterification zone preceding said final esterification zone comprises material of the vaporous product stream from the next succeeding secondary esterification zone.

17. A process according to claim 16, in which the second feed stream to the, or to each, said esterification zone preceding said final esterification zone comprises liquid condensate obtained by condensing the vaporous product stream from the next succeeding esterification zone.

18. A process according to claim 16, in which the second feed stream to the, or to each, said esterification zone preceding said final esterification zone comprises a vaporous stream obtained by compressing the vaporous product stream from the next succeeding esterification zone.

19. A process according to claim 1, in which the first liquid feed contains, in addition to monoalkyl maleate, also at least a minor amount of dialkyl maleate.

20. A process according to claim 19, in which the dialkyl maleate content of the first liquid feed is from about 60 mole % to about 80 mole %.

21. A process according to claim 1, in which the alkyl alcohol is ethanol, the monoalkyl maleate is monoethyl maleate, and the dialkyl maleate is diethyl maleate.

22. A process according to claim 34, in which monoethyl maleate produced in the monoesterification zone is reacted with ethanol in a primary esterification zone containing a charge of a solid esterification catalyst, and in which the resulting intermediate esterification product mixture is distilled in a first distillation step to separate a mixture containing ethanol and water from a mixture containing mono- and di-ethyl maleates, which mixture is used as the first liquid feed to said secondary esterification zone, if there is only one secondary esterification zone, or to the first one of said secondary esterification zones, if there is more than one said esterification zone.

23. A process according to claim 22, in which the monoethyl maleate:ethanol molar ratio of the reaction mixture supplied to said primary esterification zone is selected so that the ethanol/water mixture obtained in the first distillation step is richer in water than the azeotropic mixture which would be produced at the distillation pressure of the first distillation step.

24. A process according to claim 23, in which the ethanol/water mixture from the first distillation step is re-distilled in a second distillation step to yield overhead a mixture of ethanol and water which is drier than the ethanol/water mixture supplied to the second distillation step and as bottom product a mixture of water and a minor amount of diethyl maleate.

25. A process according to claim 24, in which a part of the overhead product from the second distillation step is subjected to dehydration to provide a dried ethanol stream for use as the second feed stream to said secondary esterification zone, if there is only one secondary esterification zone, or to the final one of said plurality of secondary esterification zones, if there is more than one said secondary esterification zone.

26. A process according to claim 25, in which dehydration is effected using a membrane or molecular sieve.

27. A process according to claim 25, in which a water enriched fraction produced as by-product in the dehydration step is recycled to the second distillation step.

28. A process according to claim 25, in which the bottom product from the second distillation step is allowed to separate into two liquid layers, and in which the resulting organic layer is recycled to the process upstream from said at least one secondary esterification zone.

29. A process according to claim 28, in which the resulting aqueous layer is used as make up water in an aqueous neutralisation zone through which the diethyl maleate product from the secondary esterification zone is passed.

30. A process according to claim 25, in which another part of the overhead product from the second distillation step is recycled to said primary esterification stage to provide make up ethanol therefor.

31. A process according to claim 22, in which the secondary esterification zone comprises a stirred tank reactor containing a charge of ion exchange resin containing sulphonic acid groups and in which the water content of the second feed stream is less than about 15 mole %.

32. A process according to claim 23, in which vaporous effluent from the secondary esterification zone is condensed and recycled to the primary esterification zone.

33. A process for the production of a dialkyl maleate which comprises:
(a) reacting maleic anhydride with an alkyl alcohol in a monoesterification zone to form monoalkyl maleate; and
(b) reacting with monoalkyl maleate said alkyl alcohol to form dialkyl maleate, wherein a first liquid feed comprising said monoalkyl maleate is supplied to a secondary esterification zone containing a charge of a solid esterification catalyst, a second feed stream comprising said alkyl alcohol is supplied to said secondary esterification zone, said secondary esterification zone being maintained at an elevated temperature sufficient to form or maintain therein a vaporous stream containing said alkyl alcohol, said first liquid feed is intimately contacted with said vaporous stream in said secondary esterification zone in the presence of said catalyst, a vaporous effluent stream is recovered from said secondary esterification zone containing in addition to alkyl alcohol vapour, also water in vapour form, said water being produced in said secondary esterification zone by esterification of said monoalkyl maleate with said alkyl alcohol, and a liquid product containing said dialkyl maleate, is recovered from the secondary esterification zone.

34. A process as claimed in claim 33, wherein the alkyl alcohol in steps (a) and (b) is ethanol, the monoalkyl maleate is ethyl maleate and the dialkyl maleate is diethyl maleate.

* * * * *